United States Patent [19]

Kiso et al.

[11] Patent Number: 4,880,942
[45] Date of Patent: Nov. 14, 1989

[54] PREPARATION OF CYCLIC CARBONATES

[75] Inventors: Yoshihisa Kiso, Iwakuni; Yuuichi Matsunaga, Kuga; Masao Imagawa, Ohtake, all of Japan

[73] Assignee: Mitsui Petrochemical Industries, Ltd., Tokyo, Japan

[21] Appl. No.: 222,414

[22] Filed: Jul. 21, 1988

[30] Foreign Application Priority Data

Jul. 22, 1987 [JP] Japan .................. 62-180984

[51] Int. Cl.$^4$ .................. C07D 317/12; C07D 323/04
[52] U.S. Cl. .................. 549/228; 549/229; 549/230
[58] Field of Search ............. 558/277; 549/228, 229, 549/230

[56] References Cited
U.S. PATENT DOCUMENTS
1,995,291  3/1935  Carothers .................. 549/228

FOREIGN PATENT DOCUMENTS
0035304  9/1981  European Pat. Off. .
58-49377  3/1983  Japan .

OTHER PUBLICATIONS

Chemical Abstracts, 93:53769g (1983) (Abstract of J.P. 58-49377).

Primary Examiner—Richard L. Raymond
Assistant Examiner—Mark W. Russell
Attorney, Agent, or Firm—Nixon & Vanderhye

[57] ABSTRACT

Cyclic carbonates are prepared by reacting a 1,3-diol or 1,2-diol with a dialkylcarbonate in the presence of a basic catalyst. They are obtained in higher yields with higher purity by subjecting the reaction mixture to heat aging under vacuum in the presence of the basic catalyst, and recovering the cyclic carbonate from the mixture.

6 Claims, 1 Drawing Sheet

PREPARATION OF CYCLIC CARBONATES

BACKGROUND OF THE INVENTION

1. Field of the Invention

This invention relates to a process for preparing cyclic carbonates from diols.

2. Prior Art

It is well known in the art to prepare cyclic carbonates from diols. For example, Japanese Pat. Application Kokai No. Sho 58-49377 (laid open on Mar. 23, 1983) discloses a process for preparing 1-isopropyl-2,2-dimethyl-1,3-propylene carbonate by heating 2,2,4-trimethyl-1,3-pentanediol and a dialkylcarbonate in the presence of a conventional esterifying catalyst such as para-toluenesulfonic acid to effect ester exchange reaction. The typical dialkylcarbonate used in examples is diethylcarbonate.

We carried out similar reaction in the presence of para-toluenesulfonic acid catalyst by substituting dimethylcarbonate for the diethylcarbonate. There was obtained only a small amount of cyclic carbonate. It was found that the reaction does not proceed smoothly with every dialkylcarbonate when a cyclic carbonate is prepared by reaction of a diol with a dialkylcarbonate in the presence of an acid catalyst such as para-toluenesulfonic acid.

Japanese Pat. Application Kokai No. Sho 56-133246 discloses a process of reacting a diallyl carbonate ester with a polyhydric alcohol such as diethylene glycol in the presence of a basic catalyst to form an allyl carbonate ester of a polyhydric alcohol. The carbonate obtained by this process is a chain carbonate such as ethylene glycol bisallyl carbonate. There are obtained no cyclic carbonates.

SUMMARY OF THE INVENTION

An object of the present invention is to provide a simple process for preparing a cyclic carbonate from a diol in a high yield with a high selectivity.

According to the present invention, there is provided a process for preparing a cyclic carbonate, comprising (a) reacting at least one diol selected from the group consisting of 1,3-diols and 1,2-diols with a dialkylcarbonate in the presence of a basic catalyst.

In one preferred embodiment of the present invention, the reaction is carried out under approximately atmospheric pressure or under pressure. The basic catalyst is selected from basic compounds of alkali and alkaline earth metals. The preferred alkyl carbonate is dimethylcarbonate.

In a further preferred embodiment of the present invention, the process further includes (b) subjecting the reaction mixture to heat aging under vacuum in the presence of a basic catalyst, and (c) isolating the resulting cyclic carbonate from the mixture. Most often, the basic catalyst used in heat aging step (b) is the same as used in reaction step (a). Heat aging under vacuum is preferably carried out at a temperature of from about 100° to about 200° C. under a vacuum of up to about 400 mmHg for a time of from about ½ to about 5 hours. More preferably heat aging is carried out while removing the generating dialkyl carbonate from the system.

BRIEF DESCRIPTION OF THE DRAWING

The above and other objects, features, and advantages of the present invention will be better understood from the following description taken in conjunction with the accompanying drawing, in which.

the only figure.

DETAILED DESCRIPTION OF THE INVENTION

Figure 1:
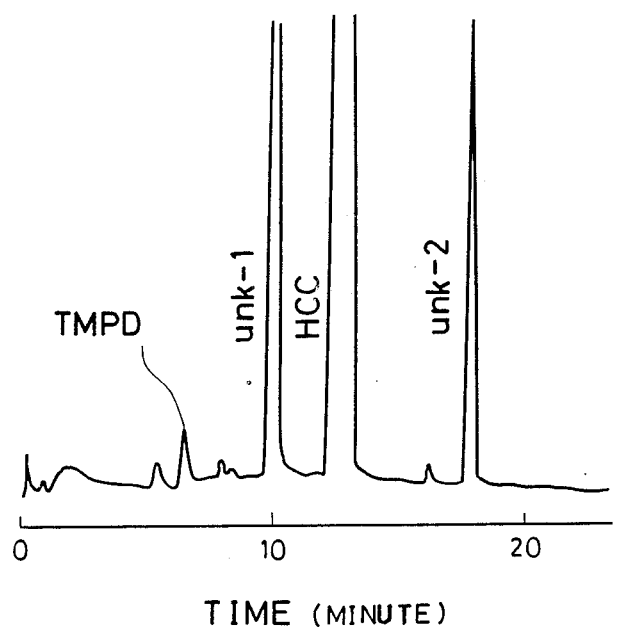
FIG. 1 is a diagram showing the gas chromatogram of a reaction mixture of a diol and a dialkylcarbonate before it is aged.

According to the process of the present invention, a cyclic carbonate is prepared by reacting at least one diol selected from the group consisting of 1,3-diols and 1,2-diols with a dialkylcarbonate in the presence of a basic catalyst.

The presence of a basic catalyst is ssential for the reaction to proceed. The basic catalysts used herein include basic compounds of alkali metals and alkaline earth metals, for example, lithium hydroxide, sodium hydroxide, potassium hydroxide, cesium hydroxide, sodium hydrogen carbonate, potassium carbonate, sodium methoxide, sodium ethoxide, sodium phenoxide, sodium acetate, sodium hydride, metallic sodium, sodium amide, butyl lithium, and calcium hydroxide; amines such as imidazole, ethylamine, and 1,8-diazabicyclo[4.5.0.]undecene-7 (DBU); and basic ion-exchange resins. Higher yields of the end product, cyclic carbonate are expected with the use of strongly basic catalysts among others. Preferred basic catalysts are basic compounds of alkali metals and alkaline earth metals, for example, are sodium hydroxide, potassium hydroxide, sodium methoxide and potassium methoxide. Most preferred are sodium hydroxide and sodium methoxide.

The basic catalyst is preferably added to the reaction mixture such that about 0.0001 to about 0.1 mol, more preferably about 0.001 to about 0.05 mol of basic catalyst is present per mol of diol.

In the practice of the present invention, the reaction may generally be carried out without solvent. If necessary, any desired solvent may be used insofar as it does not adversely affect the reaction.

The reaction between diol and dialkylcarbonate may be carried out under approximately atmospheric pressure or under pressure. Usually, the reaction is carried out under ambient or atmospheric pressure. The term approximately atmospheric pressure used herein is a pressure approximate to the atmospheric pressure and having no adverse affect on the reaction and generally encompasses pressures in the range of atmospheric pressure $\pm 10$ mmHg. Pressure may be applied during the reaction. The level of the applied pressure is not critical although generally the upper limit is 10 atmospheres. In the practice of the present invention, it is preferred to heat the reaction mixture to at least the temperature at which the alcohol formed from the reaction is distilled off. With the use of dimethylcarbonate, the reaction forms methanol which forms an azeotrope with unreacted dimethylcarbonate. It is desired to azeotropically distill the methanol out of the system during the reaction. The reaction temperature varies with the type of diol and dialkylcarbonate used, but generally ranges from about 60° to about 180° C.

The reaction time generally ranges from about ½ to about 20 hours. When reaction of diol with dialkylcarbohate is carried out under a reduced pressure lower than the approximately atmospheric pressure, one reactant, dialkylcarbonate will be distilled off at a low temperature. It may be then inconvenient to maintain the reaction temperature to the above-mentioned range.

For this reason, the reaction is carried out under approximately atmospheric pressure or under applied pressure.

In the practice of the present invention, the reactor may be charged with an entire amount of dialkylcarbonate from the first. It is also possible to charge the reactor with incremental amounts of dialkylcarbonate. The reaction may be carried out under the above-mentioned conditions while maintaining the dialkylcarbonate under reflux. However, as described above, it is desired to distill the resulting alcohol such as methanol out of the system during the reaction.

The diol used herein is selected from the group consisting of 1,3-diols and 1,2-diols. Examples of the 1,3-diols include hydrocarbon diols such as 2,2,4-trimethyl-1,3-pentanediol (to be abbreviated as TMPD), 1,3-propanediol, and 1,3-butanediol. Examples of the 1,2-diols include hydrocarbon diols such as ethylene gylcol, propylene glycol, 2,3-butanediol, and 1,2-butanediol. Preferred diols are TMPD and 2,3-butanedol with TMPD being most preferred.

The dialkylcarbonates used herein include dimethylcarbonate and diethylcarbonate although the alkyl moiety may have up to 6 carbon atoms. Dimethylcarbonate is preferred.

In the practice of the present invention, the reaction mixture may preferably contain the diol and the dialkylcarbonate in such a proportion that about 0.1 to about 10 mol, more preferably about 1 to about 2 mol of dialkylcarbonate is present per mol of diol.

The process of the present invention can produce a variety of cyclic carbonates including ethylene carbonate, 1-2-propylene carbonate, 2,3-butylene carbonate, 1,2-butylene carbonate, 1,3-propylene carbonate, and 1-isopropyl-2,2-dimethyl-1,3-propylene carbonate (to be abbreviated as HCC).

In the practice of the present invention, the cyclic carbonate may be recovered from the reaction mixture in which 1,3-diol or 1,2-diol has been reacted with dialkylcarbonate, for example, by distilling the cyclic carbonate followed by recrystallization. However, the cyclic carbonate is recovered in a low yield because the reaction mixture contains a large amount of by-products. It is therefore desirable to carry out heat aging under vacuum on the reaction mixture before the cyclic carbonate is isolated therefrom. Then the cyclic carbonate of higher purity is obtained in higher yields. The heat aging under vacuum may be carried out in a simple manner as described below.

The reaction mixture according to the present invention may be subjected to heat aging under vacuum in the presence of the basic catalyst, that is, without removing the basic catalyst which has been used in the reaction between diol and dialkyl carbonate. If necessary, an additional amc,unt of the same or different basic catalyst may be introduced. The heat aging under vacuum may be carried out by heating the reaction mixture under a vacuum to a temperature in the range of from a temperature equal to or above the boiling point of the dialkyl carbonate under the vacuum to a temperature lower than the boiling point of the intended cyclic carbonate under the vacuum while removing the dialkyl carbonate generated from by-products in the reaction mixture. While the reaction mixture contains by-products as impurities, the heat aging under vacuum of the reaction mixture converts the by-products into the intended cyclic carbonate. This conversion was discovered by the present inventors.

The vacuum used in the heat aging is a reduced pressure lower than the atmospheric pressure, preferably from 0.1 to 400 mmHg. A temperature in the range of from about 100° to about 200° C. are generally preferred although they depend on the type of reactants, diol and dialkyl carbonate. The aging time generally ranges from about ¼ to about 5 hours.

In carrying out the post-treatment or heat aging under vacuum of the reaction mixture, by-products in the reaction mixture can be very efficiently converted into cyclic carbonate when the temperature and pressure are within the above-mentioned range. The heat aging under vacuum of the reaction mixture is to convert the by-products into the intended cyclic carbonate as described above. Upon conversion, the same dialkyl carbonate as the reactant is released from the by-products. Thus heat aging under vacuum of the reaction mixture should preferably be carried out while removing the generated dialkyl carbonate from the system.

The cyclic carbonate is isolated in significantly increased yield and purity, after the reaction mixture is subjected to heat aging under vacuum. These improvements are illustrated by referring to an example of reaction using TMPD as a diol and dimethyl carbonate as a dialkyl carbonate. On analysis of the reaction mixture by gas chromatography, at least two peaks indicative of by-products (which are designated as unk-1 and unk-2 in Table 1 and FIG. 1) appear in addition to the peak indicative of the intended cyclic carbonate. Considering the results of NMR and gas mass analysis together, we suppose that these by-products have the structures:

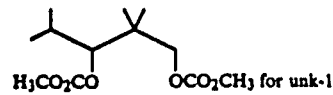

and

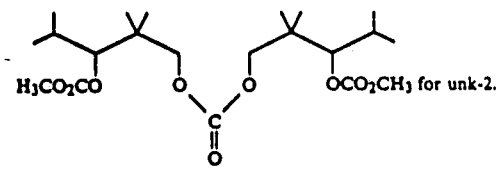

The reaction mixture contains a considerable amount of by-products. So as to obtain the cyclic carbonate in a high yield with high purity when it is isolated from the as-reacted mixture, the reaction mixture was subjected to heat aging under vacuum as mentioned above. It was observed that the peaks of unk-1 and unk-2 were decreased and the peak of the intended cyclic carbonate was increased upon heat aging under vacuum. It was also found that the same dimethyl carbonate as the reactant generated from the by-products upon heat aging under vacuum.

These results suggest that heat aging under vacuum of the reaction mixture is effective in converting by-products therein into the intended cyclic carbonate. The present invention is based on this finding. We have also found that effective conversion is not accomplished unless heat aging under vacuum is conducted in the presence of a basic catalyst. This means that the basic catalyst which is used in the reaction step prior to heat aging under vacuum need not be removed by filtration (in the case of a solid basic catalyst), neutralization, or washing. The cyclic carbonate preparation process of the present invention is thus a very simple process.

Subsequent to heat aging under vacuum, the cyclic carbonate may be isolated from the aged reaction mixture by an ordinary recovery technique such as distillation and recrystallization.

The process of the present invention is successful in producing a cyclic carbonate of high purity in a high yield in a simple manner.

The cyclic carbonates are useful in a variety of applications including organic electrolytes, ink medium, particularly as additives for special ink such as high-speed jet recording ink, reaction medium, and dispersing medium.

The gas chromatogram of the reaction mixture of Example 4 is shown in FIG. 1.

EXAMPLES

Examples of the present invention are given below by way of illustration and not by way of limitation.

EXAMPLES 1-4

A glass rotary evaporator having an interior volume of 50 liters and equippped with a reflux condenser was charged with 10.7 kg (73.3 mol) of 2,2,4-trimethyl-1,3-pentanediol (TMPD), 14.5 kg (161.1 mol) of dimethylcarbonate (DMC), and 0.03 kg (0.75 mol) of sodium hydroxide (NaOH). Reaction was carried out under atmospheric pressure at the temperature (bath temperature) for the time both shown in Table 1.

During the reaction, methanol and DMC were evaporated off from the reactor. In Examples 1 and 2, evaporated methanol and DMC were cooled and condensed in the reflux condenser and returned to the reactor. In Examples 3 and 4, after reflux operation was carried out for 6 hours, the reaction was continued without reflux operation while the condensate which consisted of unreacted DMC and methanol was distilled out of the reaction system.

After reaction was continued for a predetermined time, the reaction mixture was analyzed by gas chromatography (GC) using 2% Silion OV-225/Uniport HP column. The areas of the peaks indicative of TMPD, HCC, unk-1 and unk-2 excluding low-boiling substances such as methanol and DMC are calculated in % and reported in Table 1. An exemplary gas chromatogram is shown in FIG. 1. It is to be noted that unk-1 and unk-2 in Table 1 and FIG. 1 are as previously defined.

EXAMPLE 5

A glass flask having an internal volume of 500 ml was charged with 146 grams (1.0 mol) of TMPD, 135 grams (1.5 mol) of DMC, and 0.41 grams (0.01 mol) of NaOH. With stirring by a magnetic stirrer, reaction was carried out under atmospheric pressure at the temperature (contents temperature) for the time both shown in Table 1. Methanol which generated with the progress of reaction was distilled out along with DMC. The results are shown in Table 1.

EXAMPLE 6

The procedure of Example 5 was repeated except that the catalyst NaOH was replaced by NaOCH$_3$ and the reaction temperature (contents temperature) was set to 85° C. The results are shown in Table 1.

COMPARATIVE EXAMPLE 1

The procedure of Example 5 was repeated except that the catalyst NaOH was replaced by p-toluenesulfonic acid and the reaction temperature (contents temperature) was set to 102° C. The results are shown in Table 1.

TABLE 1

| Example | Catalyst | Reaction Time (hr) | Temp* (°C.) | Composition (GC area in %) | | | | TMPD conversion (%) | HCC yield (%) |
|---|---|---|---|---|---|---|---|---|---|
| | | | | TMPD | unk-1 | HCC | unk-2 | | |
| 1 | NaOH | 2 | (130) | 54.7 | 1.3 | 43.6 | 0.0 | — | — |
| 2 | NaOH | 6 | (130) | 23.6 | 4.6 | 70.9 | 0.2 | — | — |
| 3 | NaOH | 8 | (127) | 7.6 | 6.7 | 84.5 | 0.4 | — | — |
| 4 | NaOH | 12 | (144) | 0.7 | 14.5 | 82.6 | 1.8 | about 100 | 88.4 |
| 5 | NaOH | 5 | 95 | 0.3 | 14.3 | 80.9 | 3.6 | about 100 | 86.6 |
| 6 | NaOCH$_3$ | 5 | 85 | 24.3 | 5.0 | 70.4 | 0.3 | 72.6 | 67.1 |
| CE1 | p-toluene-sulfonic acid | 5 | 102 | 97.3 | 0.0 | 2.4 | 0.0 | 2.7 | 2.4 |

*temperature in parentheses is a bath temperature.

EXAMPLES 7-9

The reaction mixture obtained in Example 4 was subjected to heat aging under vacuum without removing the basic catalyst NaOH therefrom. The temperature, pressure, and time used in the heat aging under vacuum are reported in Table 2. During aging, DMC released was distilled out of the system. The results are shown in Table 2.

In all the examples, the compounds identified as unk-1 and unk-2 disappeared and the amount of the end product, 1-isopropyl-2,2-dimethyl-1,3-propylene carbonate (HCC) was increased at the end of heat aging under vacuum of the reaction mixture in the presence of the catalyst NaOH.

COMPARATIVE EXAMPLE 2

In the reaction mixture composed of the composition reported in Table 2, the catalyst NaOH used in the reaction was neutralized with 1N NH$_4$Cl before the reaction mixture was subjected to heat aging under vacuum at 150° C. and 15 mmHg for 2 hours. The results are shown in Table 2.

COMPAIRATIVE EXAMPLE 3

A reaction mixture of the composition reported in Table 2 having a high concentration of unk-1 was prepared without adding a basic catalyst. It was subjected to heat aging under vacuum at 150° C. and 15 mmHg for 2 hours, with the results shown in Table 2.

EXAMPLE 10

To the same reaction mixture as used in Comparative Examlle 3 was added 0.1% by weight of NaOH. It was subjected to heat aging under vacuum at 150° C. and 15 mmHg for 2 hours, with the results shown in Table 2.

TABLE 2

| | Example 7 | | Example 8 | | Example 9 | | CE 2 | | CE 3 | | Example 10 | |
|---|---|---|---|---|---|---|---|---|---|---|---|---|
| Aging* | | | | | | | | | | | | |
| Temperature | 150° C. | | 165° C. | | 150° C. | | 150° C. | | 150° C. | | 15 mmHg | |
| Vacuum | 15 mmHg | | 30 mmHg | | 200 mmHg | | 15 mmHg | | 15 mmHg | | 2 hours | |
| Time | 2 hours | | 4 hours | | 2 hours | | 2 hours | | 2 hours | | | |
| Composition (grams) | Charge | Aged | Charge | Aged | Charge | Aged | Charge | Aged | Charge | Aged | Charge | Aged |
| TMPD | 0.12 | 0.0 | 0.13 | 0.41 | 0.13 | 0.69 | 0.32 | 0.34 | 1.75 | 1.75 | 1.75 | 0.41 |
| unk-1 | 12.96 | 0.07 | 13.71 | 0.51 | 13.62 | 0.49 | 8.20 | 8.14 | 32.62 | 32.62 | 32.62 | 0.24 |
| HCC | 73.87 | 85.79 | 78.12 | 90.12 | 77.63 | 90.72 | 43.56 | 44.58 | 60.36 | 60.36 | 60.36 | 80.58 |
| unk-2 | 2.33 | 0.0 | 2.46 | 0.12 | 2.45 | 0.04 | 2.07 | 2.07 | — | — | — | — |
| others | 7.3 | — | 7.7 | — | 7.7 | — | 5.9 | — | 5.27 | — | 4.8 | — |
| Total | 96.58 | 85.86 | 102.14 | 94.01 | 101.50 | 96.61 | 60 | 59.56 | 100 | 99.56 | 99.5 | 85.4 |
| Distillate (grams) | | 7.71 | | 6.69 | | 5.66 | | 0.45 | | 0.5 | | 15.4 |

*Heat aging under vacuum was carried out in the presence of NaOH in Examples 7-9 and 10, but in the absence of NaOH in Comparative Examples 2 and 3.

EXAMPLE 11

The reaction mixture obtained in Example 5 was subjected to heat aging under vacuum at 150° C. and 15 mmHg for 2 hours. The end product HCC was recovered by simple batch distillation under a vacuum of 5 mmHg at a column top temperature of 123° C. The conversion of TMPD was 100%. The isolation yield was 95.4% as expressed in % by the amount (grams) of HCC isolated by distillation divided by the theoretical (grams). The resulting HCC was 99.6% pure.

EXAMPLE 12

A glass flask having an internal volume of 3 liters was charged with 900 grams (10 mol) of 2,3-butylene glycol (BG), 1350 grams (15 mol) of DMC, and 4 grams (0.1 mol) of NaOH. With stirring by a magnetic stirrer, reaction was carried out under atmospheric pressure at a temperature (contents temperature) of 100° C. for 8 hours. Methanol which generated with the progress of reaction was azeotroped off with DMC. At the end of reaction, the reaction mixture was subjected to heat aging under vacuum at 120° C. and 15 mmHg for 2 hours without removing the basic catalyst NaOH therefrom. The end product, 2,3-butylene carbonate (2,3-BC) was recovered by simple batch distillation. The conversion of BG was 100%. The isolation yield was 97.5% as expressed in % by the amount (grams) of 2,3-BC isolated by distillation divided by the theoretical (grams). The resulting 2,3-BC was 99.9% pure.

It is seen that by-products unk-1 and unk-2 in the reaction mixture resulting from reaction of TMPD and dimethylcarbonate reactants to synthesize HCC can be converted into the end product HCC by subjecting the reaction mixture to heat aging under vacuum in the presence of a basic catalyst. The same applies to any other combinations of diol, dialkylcarbonate, and basic catalyst.

Obviously, numerous modifications and variations of the present invention are possible in light of the above teachings. It is therefore to be understood that within the scope of the appended claims, the invention may be practiced otherwise than as specifically described herein.

We claim:

1. A process for preparing a cyclic carbonate, comprising the steps of:
   reacting at least one diol selected from the group consisting of 1,3-diols and 1,2-diols with a dialkylcarbonate in the presence of a basic catalyst under approximately atmospheric pressure or under pressure,
   subjecting the reaction mixture to heat aging under vacuum in the presence of a basic catalyst, and
   isolating the resulting cyclic carbonate from the mixture.

2. The process of claim 1 wherein the basic catalyst used in the heat aging step is the basic catalyst which has been used in the said reaction of claim 1 and remains in system without being removed after the reaction.

3. The process of claim 1 or 2 wherein said basic catalyst is a basic compound of an alkali or alkaline earth metal.

4. The process of claim 1 or 2 wherein the dialkylcarbonate is dimethylcarbonate.

5. The process of claim 1 or 2 wherein the aging is carried out at a temperature of from about 100° to about 200° C. under a vacuum of from about 0.1 to about 400 mmHg for about ½ to about 5 hours.

6. The process of claim 1 or 2 wherein the aging is carried out while removing the generated dialkyl carbonate from the system.

* * * * *